(12) United States Patent
Watts et al.

(10) Patent No.: US 11,890,000 B2
(45) Date of Patent: Feb. 6, 2024

(54) CERVICAL RETRACTOR AND METHOD

(71) Applicants: Charles R. Watts, Hopkins, MN (US); Paul A. James, Edina, MN (US)

(72) Inventors: Charles R. Watts, Hopkins, MN (US); Paul A. James, Edina, MN (US)

( * ) Notice: Subject to any disclaimer, the term of this patent is extended or adjusted under 35 U.S.C. 154(b) by 24 days.

(21) Appl. No.: 17/656,823

(22) Filed: Mar. 28, 2022

(65) Prior Publication Data

US 2022/0218324 A1  Jul. 14, 2022

Related U.S. Application Data

(63) Continuation of application No. 16/949,144, filed on Oct. 15, 2020, now Pat. No. 11,311,282.

(51) Int. Cl.
*A61B 17/02* (2006.01)

(52) U.S. Cl.
CPC ........ *A61B 17/025* (2013.01); *A61B 17/0206* (2013.01); *A61B 2017/0256* (2013.01)

(58) Field of Classification Search
CPC .............. A61B 17/0206; A61B 17/025; A61B 2017/0256
See application file for complete search history.

(56) References Cited

U.S. PATENT DOCUMENTS

| | | | |
|---|---|---|---|
| 5,052,373 A | 10/1991 | Michelson | |
| 5,795,291 A | 8/1998 | Koros et al. | |
| 6,296,609 B1 | 10/2001 | Brau | |
| 7,494,463 B2 | 2/2009 | Nehls | |
| 7,905,840 B2 | 3/2011 | Pimenta et al. | |
| 8,137,284 B2 | 3/2012 | Miles et al. | |
| 8,449,463 B2 | 5/2013 | Nunley et al. | |
| 8,876,904 B2 | 11/2014 | Pimenta et al. | |
| 9,113,853 B1 | 8/2015 | Woolley et al. | |
| 10,098,622 B2 | 10/2018 | Seex | |
| 10,285,680 B2 | 5/2019 | Friedrich et al. | |
| 10,426,454 B2 | 10/2019 | Ponmudi et al. | |
| 2005/0192484 A1 | 9/2005 | Sharratt et al. | |
| 2011/0137130 A1* | 6/2011 | Thalgott | A61B 1/32 600/232 |
| 2014/0031874 A1 | 1/2014 | Kucharzyk et al. | |
| 2019/0015089 A1 | 1/2019 | Rosenbaum et al. | |
| 2020/0113713 A1 | 4/2020 | Lamarca et al. | |

OTHER PUBLICATIONS

U.S. Appl. No. 16/949,144, filed Oct. 15, 2020, Cervical Retractor and Method.
"U.S. Appl. No. 16/949,144, Notice of Allowance dated Dec. 29, 2021".
"U.S. Appl. No. 16/949,144, Response filed Nov. 17, 2021 to Restriction Requirement dated Nov. 12, 2021".

(Continued)

*Primary Examiner* — Samuel S Hanna
(74) *Attorney, Agent, or Firm* — Schwegman Lundberg & Woessner, P.A.

(57) ABSTRACT

A retractor blade includes a shaft having a head portion at a first end and a foot portion at a second end of the shaft. A connector is coupled to the head portion for coupling to a frame. A toe portion extends from the foot portion and has a width and longitudinal curvature configured to at least partially conform to a curvature of a spinal vertebral body.

13 Claims, 13 Drawing Sheets

(56) References Cited

OTHER PUBLICATIONS

"U.S. Appl. No. 16/949,144, Restriction Requirement dated Nov. 12, 2021".

"Cervical Retractor Set for Spinal Surgery", Renix International (2020); retrieved from https://www.alibaba.com/product-detail/cervical-retractor-set-for-spinal-surgery_50032240132.html, (2020), 3 pgs.

"LITe Midline Retractor", Stryker (2016); retrieved at: https://www.tedansurgical.com/literature/phantom-Is-mini-lumbar-retractor-system/, (2016), 4 pgs.

"Phantom LS Mini Lumbar Retractor System", TeDan Surgical Innovations (2020); retrieved at: https://www.tedansurgical.com/literature/phantom-Is-mini-lumbar-retractor-system/, (2020), 6 pgs.

* cited by examiner

# CERVICAL RETRACTOR AND METHOD

CROSS-REFERENCE TO RELATED APPLICATIONS

This application is a continuation of U.S. Ser. No. 16/949,144, filed 15 Oct. 2020, the benefit of priority of which is claimed herein and which application is hereby incorporated by reference herein in its entirety.

BACKGROUND

Prior cervical retractor blades typically rely on placement of a distal portion or lip of the retractor blade underneath the longitudinal fibers of the longus coli over the transverse processes of the vertebral body to maintain alignment of the retractor. This provides only one point of anatomic fixation (fibers of longus coli) other than the retractor body. Although the retractor blades are ideally positioned on the anterior surface of the respective vertebral bodies' transverse processes, the conformation of the blade is such that it does not actively engage the bony structures.

It should also be noted that the fibers of longus coli are elastic and provide little to no fixation to the blade. This lack of fixation, along with the gentle upward slope of the transverse processes, tend to cause the retractor blade to slip from its initial placement by either rotating, slipping, or angling in such a way that the ideal surgical corridor to the vertebral bodies and the associated disc space can be significantly compromised.

The elastic nature of the longus coli fixation also means that it is difficult to obtain true midline anterior posterior visualization of the disc space and the associated exiting nerve roots of the vertebral body. The retractor blades are also deficient in that if complete removal of the uncinate processes/uncal vertebral joint is desired, the retractor blades do not provide protection of the vertebral arteries and the exiting nerve roots.

SUMMARY

A retractor blade includes a shaft having a head portion at a first end and a foot portion at a second end of the shaft. A connector is coupled to the head portion for coupling to a frame. A toe portion extends from the foot portion and has a width and longitudinal curvature configured to at least partially conform to a curvature of a spinal vertebral body and its associated uncinate processes and uncal vertebral joint.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural changes may be made without departing from the scope of the present invention. The following description of example embodiments is, therefore, not to be taken in a limited sense, and the scope of the present invention is defined by the appended claims.

A surgical corridor is a region of space created by a surgeon running from the surface (skin) to the operative target (vertebral bodies and disc space) that allows for safe retraction of surrounding tissues, optimal visualization of the desired target and associated pathology, and minimal risk of damage to adjacent vital structures. For anterior approaches to the cervical spine, this corridor is perpendicular to the anterior surfaces of the cervical-x and cervical-y vertebral bodies and parallel to the plane of the cervical-x-cervical-y disc space allowing for complete visualization of the target pathology.

Figure 1:
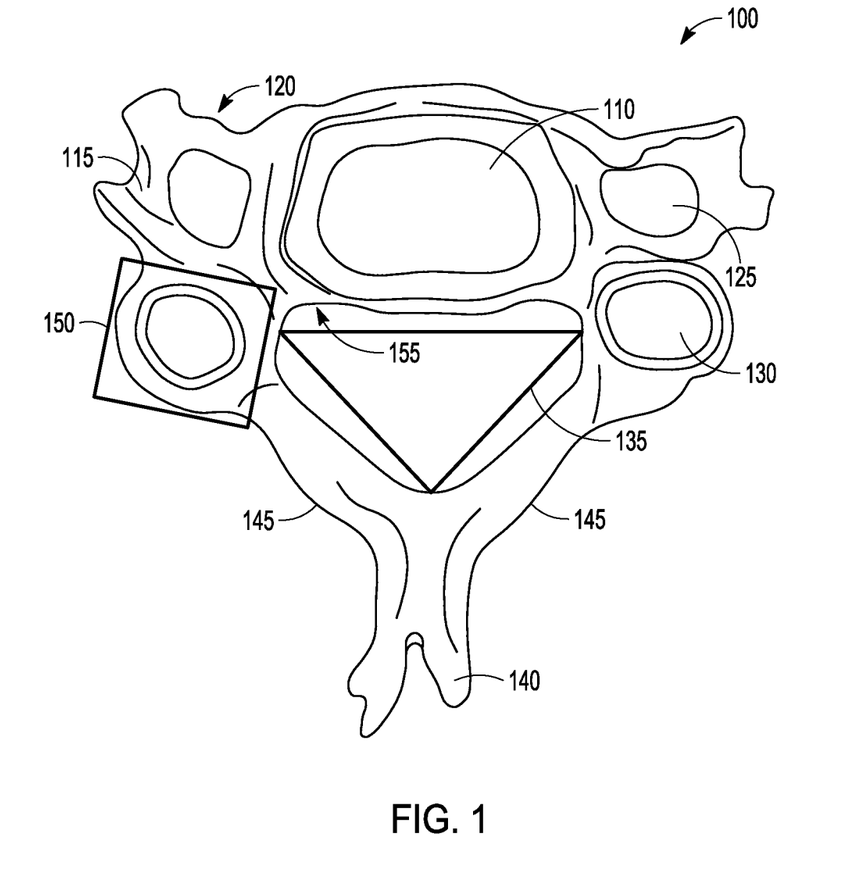
FIG. 1 is an axial view of a cervical vertebral body representative of cervical 3 through cervical 7 of a human spine.
Figure 2:
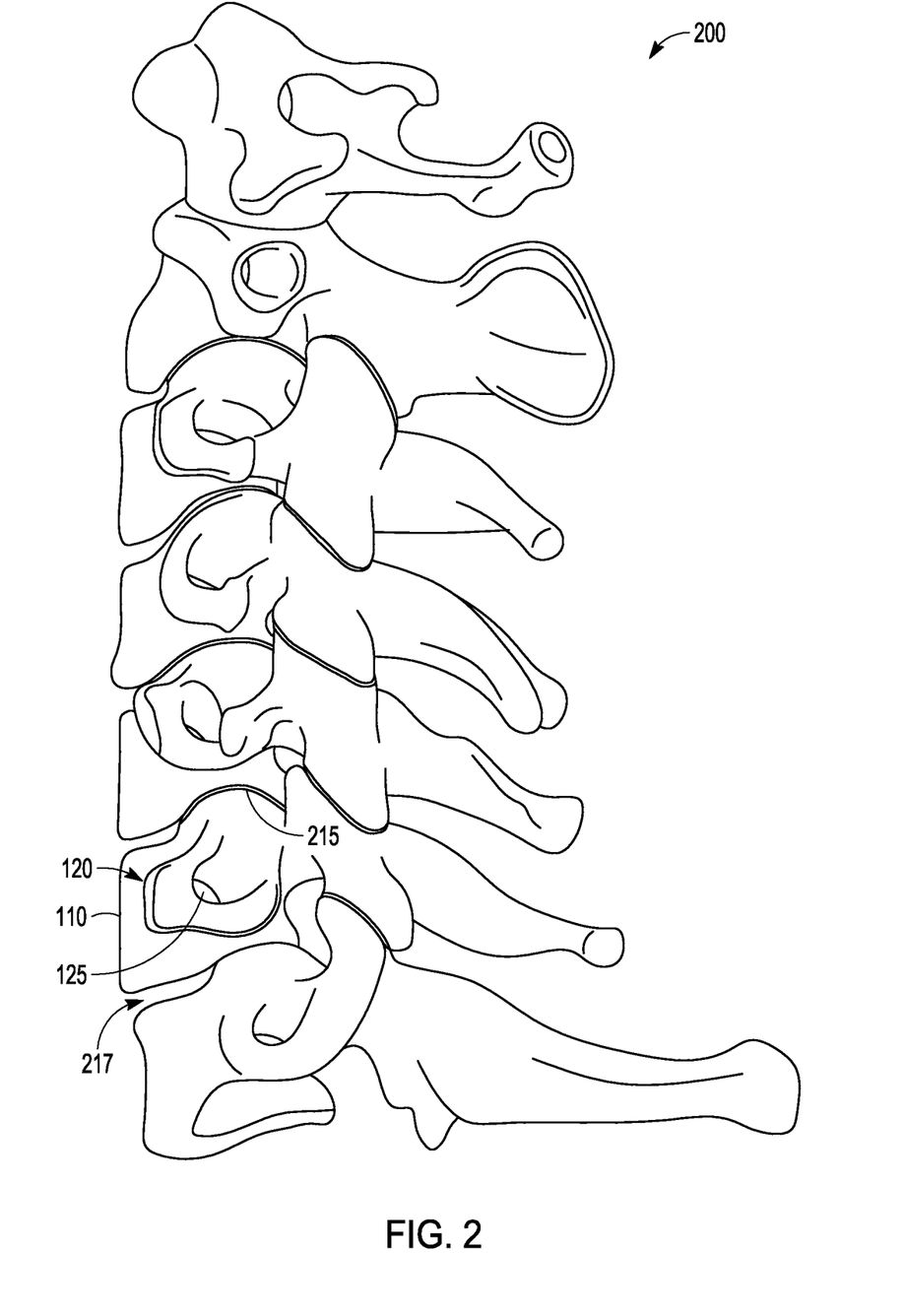
FIG. 2 is a lateral or sagittal view of the cervical spine demonstrating the location of the transverse process
Figure 3:
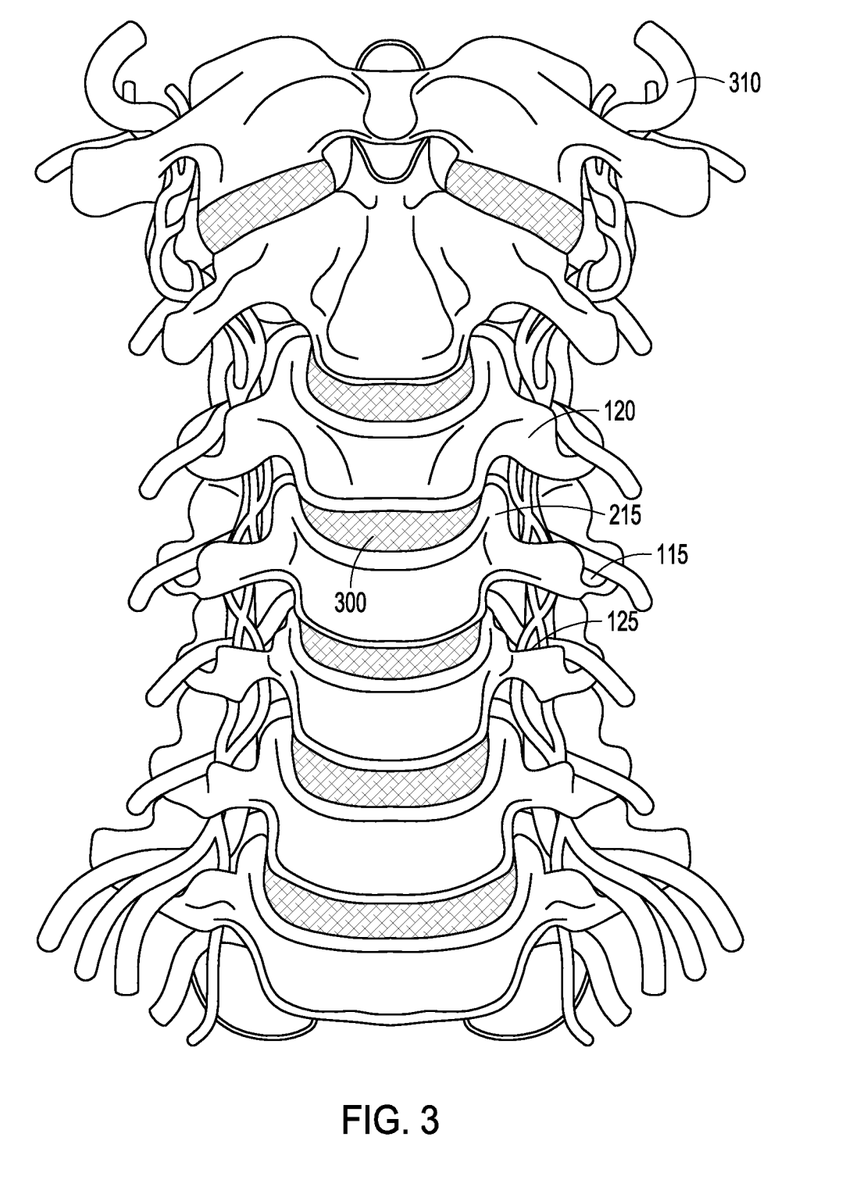
FIG. 3 is a coronal view of the cervical spine demonstrating the location of the disc and uncinated process.

FIGS. 1, 2, and 3 provide various views of a portion of a human spine, in particular, the cervical spine with labels to provide a reference for the terminology and attachment points for one or more retractor blades described herein.

FIG. 1 is an axial view of a cervical vertebral body 100 representative of cervical 3 through cervical 7 of a human spine. FIG. 1 is labeled with several terms that describe various portions of the cervical vertebral body 100. Included labeled portions include the following terms: Sulcus for spinal nerve 115, transverse process 120 (visible in FIG. 2), transverse foramen 125, superior articular facet 130, vertebral foramen 135, bifid spinous process 140, lamina 145, lateral mass 150, and bilateral pedicles 155. Note that the vertebra foramen 135 is a triangular shaped opening (triangle 135 added for illustration purposes only) formed by the lamina 145, bilateral pedicles 155, and body 110.

FIG. 2 is a lateral or sagittal view of the cervical spine 200 demonstrating the location of the transverse process 120 which contains the vertebral artery foramen 125 and vertebral artery (shown in FIG. 3) as well as the location of the uncinate process/uncal vertebral joint 215 and its relationship to the disc space 217 and neuroforamen as illustrated in FIG. 3.

FIG. 3 is a coronal view of the cervical spine 200 demonstrating the location of the disc 300, the uncinated process 215, vertebral artery 310, and nerve root with various nerves C1-C8.

In various embodiments, two different types of surgical retractor blades are used to retract soft tissue of a patient to provide a surgical corridor through anterior skin, subcutaneous tissues, and platysma muscle of the patient while protecting the strap muscles, trachea, esophagus and contents of the carotid sheath. The blades provide access to an anterior portion of the cervical spine. In other words, from the front of the patient to the spine. A medial/lateral blade retracts soft tissue elements in a direction that is perpendicular to the longitudinal axis of the spine with multi-point fixation. A cranial/caudal blade is used to retract soft tissue elements in a direction that is parallel to the longitudinal axis of the spine.

Figure 4A:
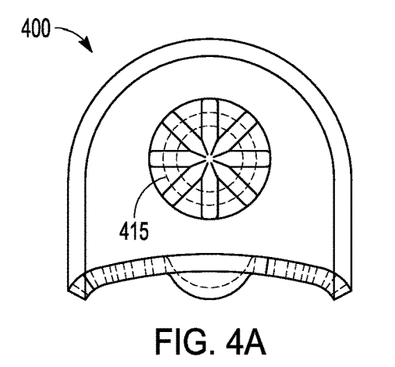
FIGS. 4A, 4B, and 4C are top, front elevation, and side elevation views respectively of a medial/lateral blade according to an example embodiment.
Figure 4B:
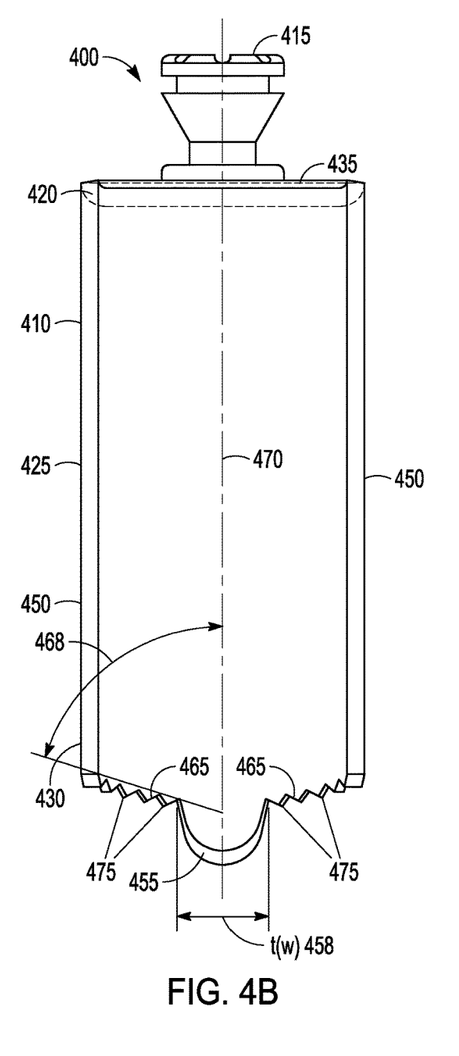
Figure 4C:
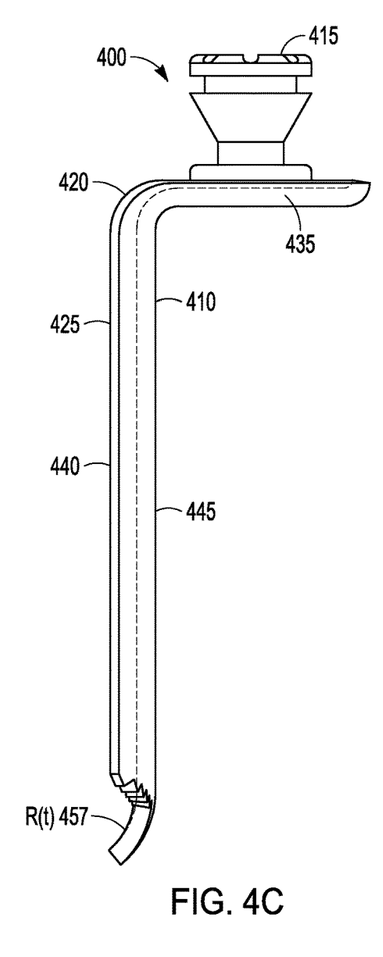

FIGS. 4A, 4B, and 4C are top, front elevation, and side elevation views respectively of a medial/lateral blade 400. Blade 400 includes a body 410 and a pin 415 attached to a head 420 of the body 410. Body 410 is a compound planar surface that can be made of various metal, plastic, or ceramic materials and compounds (including fiber or mineral reinforced compounds). The shape and form of the body 410 can be achieved by many fabrication processes including but not limited to machining, forming, casting, molding, etc. The pin 415 in one embodiment is a mostly symmetrical torus shaped feature that can be made of various metal, plastic, or ceramic materials. The shape and form of the pin 415 can be achieved by many fabrication processes including but not limited to machining, casting and molding. The body 410 and pin 415 can be made separately and then joined to make an assembly (mechanical or chemical connection/attachment), or they can be made as a single part of a single material type.

Body 410 may be formed of a single piece or multiple pieces that includes regions comprising the head 420 transitioning into a shaft 425 that further transitions into a foot 430. Each region is configured to perform various functional aspects of providing a surgical corridor.

The head 420 includes an upper portion of the body 410, called a shoulder 435 that extends away from the shaft 425 approximately 20 mm to support the mounting pin 415. A center of the shoulder 435 is a generally flat planar surface that extends generally 90 degrees from the shaft 425 of the body 410. The outside edges of the shoulder 435 may be formed with compound curved surfaces shaped to reduce stress concentrations when bearing against body tissues. The shoulder 435 supports the pin which is generally centered on the surface of the shoulder 435.

The pin 415 is shaped such that it allows for the connection of a blade to secondary retractor frame devices such as one shown in a later figure. Such frame devices may be pre-existing and utilize similar connecting pins which are specific to respective frame suppliers. The area of the body 410 where the shoulder 435 transitions to the shaft 425 may be smooth radiused, and without sharp edges or protrusions so as not to hinder access and free motion of surgical tools.

The shaft 425 region of the body 410 is a single-curved surface in one embodiment, with common thickness, that is symmetrical along its length. The shaft 425 can vary in length and width according to various use scenarios with common lengths varying between 30 to 70 mm, and widths of approximately 25 mm. In some embodiments, the width may very between 20 and 30 mm. Narrower widths might cause more injury to retracted tissue, while larger widths may also cause injury.

In one embodiment, a front surface 440 of the shaft 425 has a transverse concave curvature. A back surface 445 has a transverse convex curvature and is generally of uniform thickness and offset. The back surface 445 engages soft tissue during retraction in use. The cross-section shape of the curvature accelerates (has a shorter radius of curvature) near the sides so as to create a back 445 surface contour that reduces localized stress concentrations when bearing against body tissues. The back surface 445 contour and accelerated curvatures proximate the sides 450 effectively minimize the chances that sharp edges on the sides 450 of the shaft 425 adversely press against or otherwise engage body tissue during retraction of the tissue.

The foot 430 on the medial/lateral blade 410 begins as a continuous extension of the surfaces and sides of the shaft 425. The foot 430 terminates in a toe 455. Toe 455 maintains the transverse curvature of the shaft 425, and also longitudinally curves away from the back 445 towards the front 440 of the shaft 425. Such curvatures are referred to as a symmetrical compound (double-curved) surface curving towards the front 440 concave surface of the shaft 425. The foot 430 shape provides two functional features.

Toe 455 has a radius of curvature R(t) 457 that may be formed to fit over the uncinate process and uncovertebral joint to engage and/or at least partially conform to the uncinate process. In one embodiment, the curvature of the toe is configured to at least partially conform to a curvature of a spinal vertebral body. Example radii of curvature R(t) may vary from 5 to 30 mm.

The toe 455 is a narrow semi-elliptical protuberance which is centrally located between the extended shaft 425 sides 450, and a bridge 465 which consists of two symmetrical, generally linear-shaped edge sections 465 that connect either side of the beginning of the toe 455 with the extended sides 450 of the shaft 425. The toe 455 has a width, t(w) indicated at 458 that may vary from 4 to 10 mm. A distal end of the toe 455 is rounded in one embodiment. The Toe 455 has edges 470 that are radiused and smooth in one embodiment. An angle 468 of the bridge edge sections 465 relative to a centerline 470 of the front of the body can vary between roughly 60 and 100 degrees.

The bridge edge sections 465 may be textured with a plurality of grooves, ridges, serrations, bumps, etc. on distal ends of the bridge sections 465 in order to engage the spine and produce traction and resist sliding along the bone structure against which it rests. In one embodiment, the texture comprises triangular shaped teeth 470.

The toe 455 and bridges 465 function together to produce a secure multipoint stabilizing foundation for the blade 400 with respect to a section of a spine. These anatomical points of bony and elastic fixation include but are not limited to: the curvature of the vertebral body, the anatomy of the lateral aspects of the cervical x-cervical y uncinate processes and uncovertebral joint, the anterior aspects of the cervical x and cervical y transverse processes, and the fibers of the longus coli muscle. The toe 455 of the medial/lateral blade 400 is also designed to protect the vertebral artery and exiting nerve root if complete resection of the uncinate process/uncovertebral joint is desired.

The retractor blade 400 does not violate the disc space but is designed to use a combination of bony and soft tissue anatomy to optimize visualization of the disc space. This involves a contoured tip to engage the uncinate process/uncal vertebral joint as well as the teeth on the adjacent areas designed to engage the transverse processes combined with the elastic properties of the longus colli muscles to provide counter fixation. These engagement points provide a triangular type fixation that gives high quality visualization of the disc space and minimizes the movement of the retractor blade, thus providing a stable surgical corridor. The contours also protect the nerve and vertebral artery without incurring direct pressure or retraction of these structures.

Figure 5A:
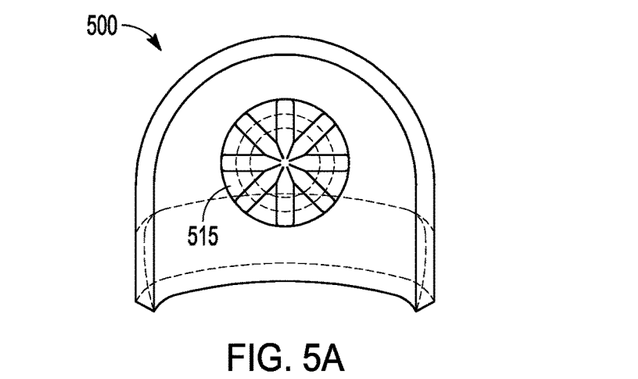
FIGS. 5A, 5B, and 5C are top, front elevation, and side elevation views respectively of a cranial/caudal blade according to an example embodiment.
Figure 5B:
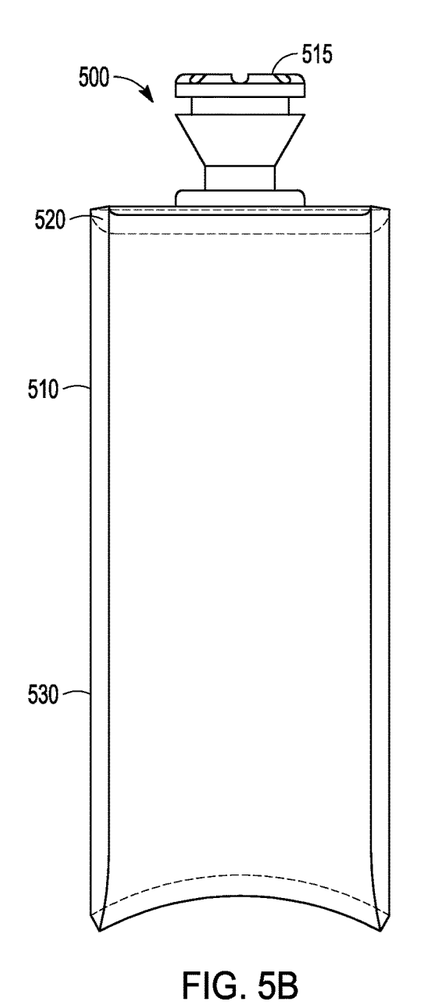
Figure 5C:
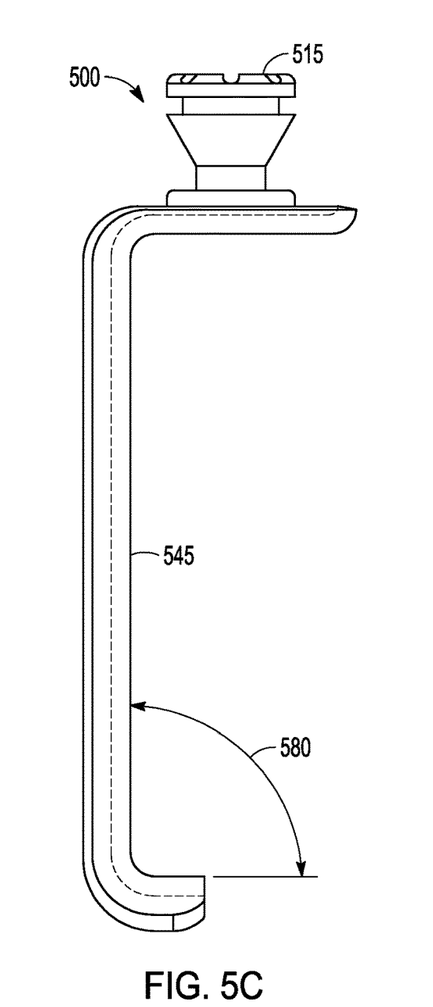

FIGS. 5A, 5B, and 5C are top, front elevation, and side elevation views respectively of a cranial/caudal blade 500. Blade 500 includes a body 510 and a pin 515 attached to a head 520 of the body 510.

Body 510 may be formed of a single piece or multiple pieces that includes regions comprising the head 520 transitioning into a shaft 525 that further transitions into a foot 530. Each region is configured to perform various functional aspects of providing a surgical corridor. The head 520 and shaft 510 regions may be the same as the head 420 and shaft 410 of blade 400 in some embodiments. The length of the blade 500 may also match or be close to the length of blade 400 during use with a fixture to hold multiple blades in place. Note also that commercially available cranial/caudal blades may be used with blades 400 in some embodiments.

The foot 530 region of blade 500 begins as a continuous extension of the surfaces and edges of the shaft 510. The foot 530 region terminates in a symmetrical double-curved (compound) surface curving towards the convex side, back side 545 of the shaft 510. The end of the foot 530 region is a smooth concave shape allowing it to slide over the generally convex surfaces of the vertebral body while preventing in pouching of soft tissues such as the esophagus and the omohyoid muscle. An angle (b) indicated at 580 between a centerline of the end of the foot region with a centerline of the shaft 545 region can vary roughly between 90 and 135 degrees.

While one or more blades 400 may be placed longitudinally to the spine with the toe 455 engaging the curvature of the vertebral body to provide lateral retraction, blades 500 may be placed perpendicular to the spine over the vertebra bodies to provide superior and inferior retraction of soft tissue to create the surgical corridor. The overall length, width, and depth of the blades 400 and 500 can vary in order to optimize their functionality for specific cervical locations and surgical procedures.

Figure 6A:
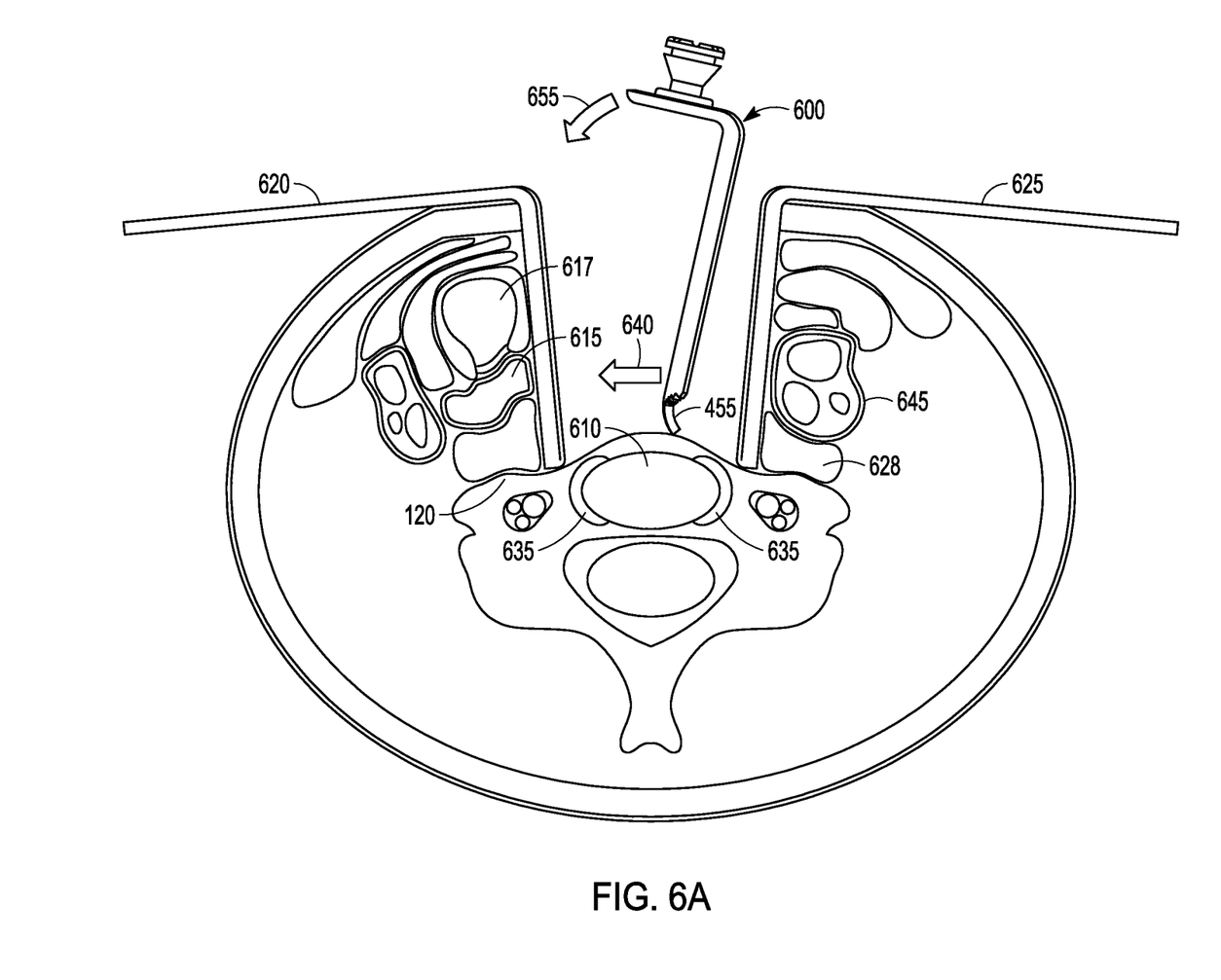
FIGS. 6A and 6B are cross section representations of a portion of spine illustrating a method of using medial/lateral retractor blades according to an example embodiment.
Figure 6B:
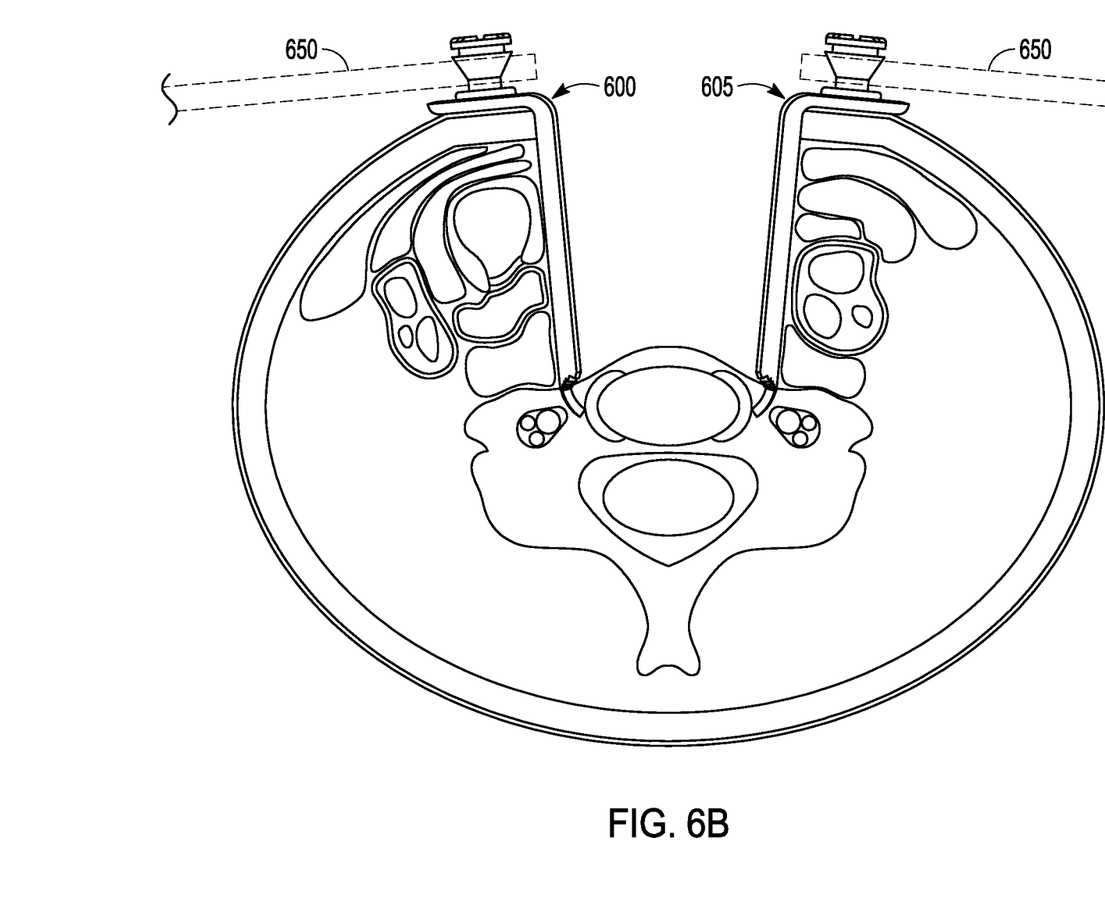

Procedural Description:

FIGS. 6A and 6B are cross section representations of a portion of spine illustrating a method of using medial/lateral retractor blades 600 and 605 corresponding to blade 400 and using reference numbers consistent with the prior description of blade 400. After obtaining access to the anterior cervical spine, the desired cervical x-cervical y disc space (where x is the associated vertebral body 610 located cranial or superior to the disc, cervical 2 through cervical 7 and y is the associated vertebral body (not visible) located caudal or inferior to the disc, cervical 3 through thoracic 1) is identified radiographically and marked. The mesial structures (those located opposite the surgeon) consisting of but not limited to the esophagus 615, trachea 617, and recurrent laryngeal nerve are gently retracted using temporary retractor devices 620, 625.

Longus coli 628 insertions are removed from the bilateral lateral aspects of the cervical x and cervical y vertebral bodies and the bilateral anterior aspects of the associated transverse processes of the cervical x and cervical y vertebral bodies exposing the cervical x-cervical y uncovertebral joint and uncinate processes 635. Starting with placement of retractor blade 400 opposite the surgeon, the toe of the medial/lateral retractor blade 400 is advanced across the surface of the cervical x-cervical y disc space moving from medial to lateral at approximately a 45 to 75 degree angle crossing over the lateral aspect of the cervical x-cervical y disc space as shown by arrow 640, finally passing over the uncinate process 635 and uncovertebral joint to rest within the space between the cervical x and cervical y transverse processes, at least partially engaging the lateral aspect of the uncovertebral joint so that the bridges 445 of the foot 430 rest on and engage the associated transverse processes 120 The curvature of the blade need not precisely match the corresponding curvature of the uncinate process.

The process is repeated for a second medial/lateral retractor blade 400 that is proximal to the surgeon taking care to protect the contents of the carotid sheath 645. The retractor blades are then connected to retraction frame arms 650 with tissue further retracted as indicated by arrow 655. If desired, blades 500 that are parallel to the cervical x-cervical y disc space can be placed and secured to their respective retraction frame arms 650, not shown. The retraction frame may be of a variety of types and configurations.

Figure 7:
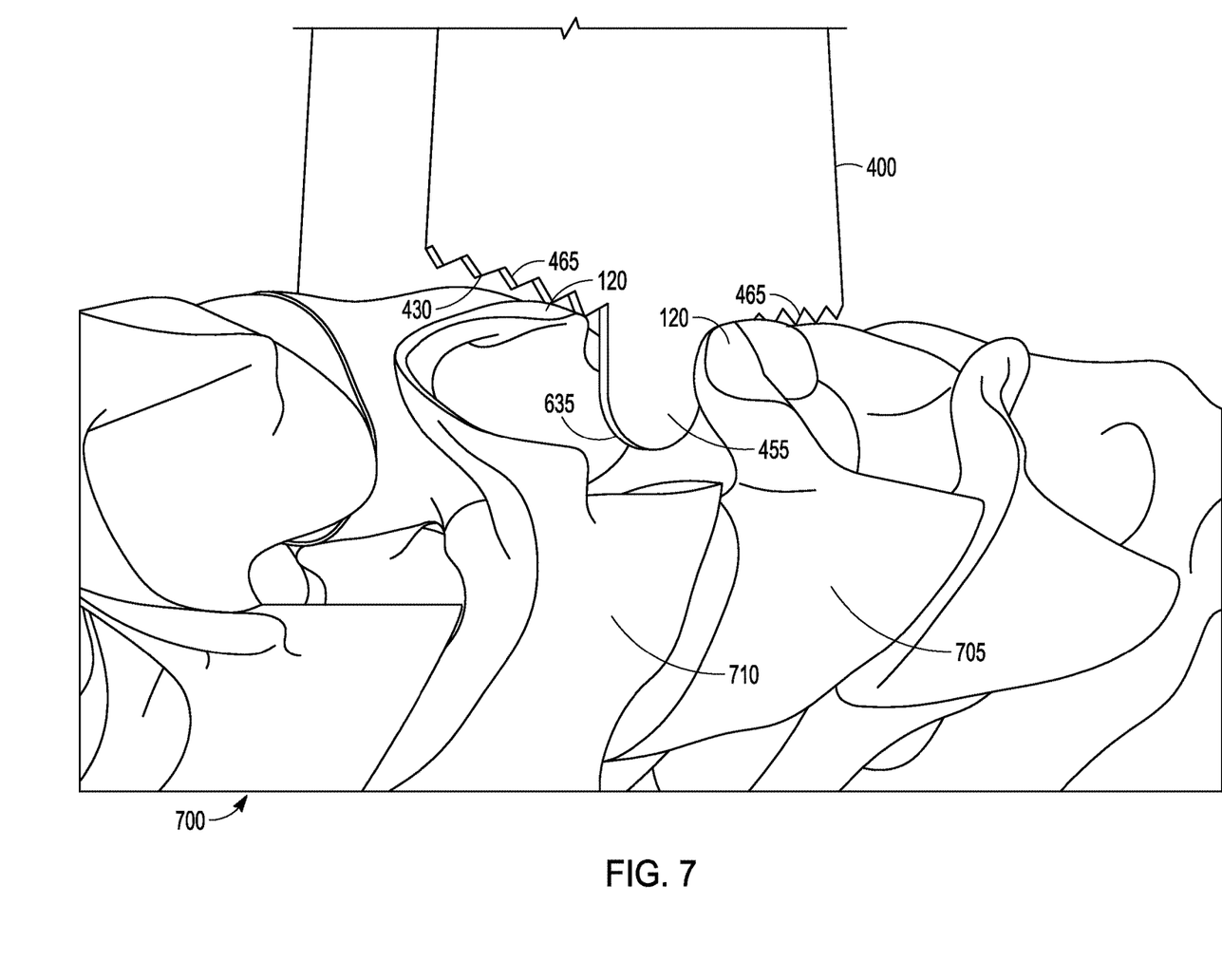
FIG. 7 is a side elevation illustrating a portion of a spine with an installed medial/lateral blade according to an example embodiment.

FIG. 7 is a side elevation illustrating a portion of a spine 700 with an installed blade 400. The toe 455 passes over the uncinate process 635 and uncovertebral joint to rest within the space between the cervical x 705 and cervical y 710 transverse processes 120, engaging the lateral aspect of the uncovertebral joint so that the bridges 465 of the foot 430 rest on and engage the associated transverse processes 120. The toe 455 is thus disposed between adjacent vertebral bodies 705 and 710 to provide a fixation point that does not damage the spine and ensures that the blade 400 stays in retentive contact with the spine 700.

Figure 8:
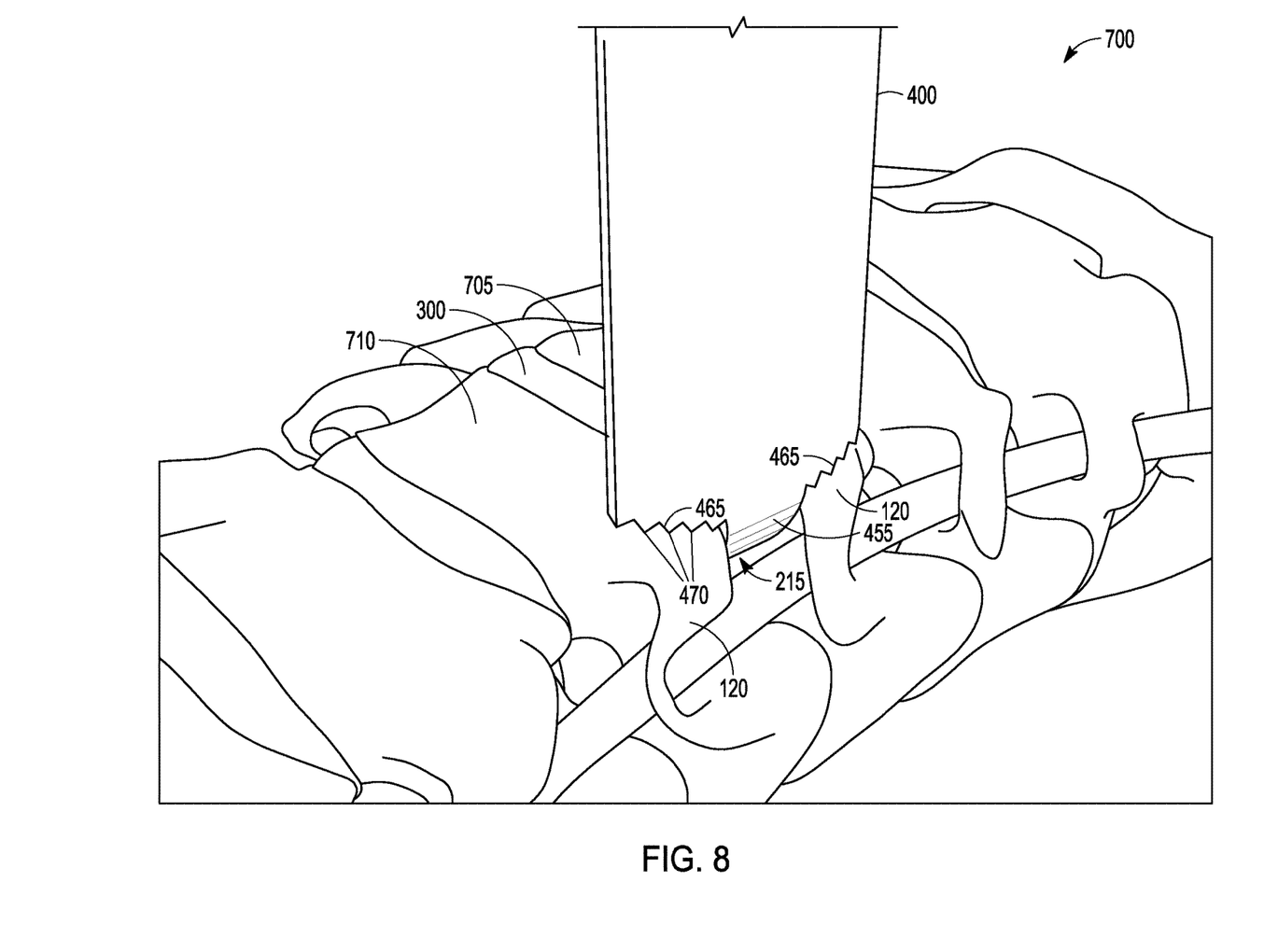
FIG. 8 is a perspective view of the spine with medial/lateral blade installed according to an example embodiment.

FIG. 8 is a perspective view of the spine 700 with blade 400 installed. Reference numbers are consistent with those used in FIG. 7.

Figure 9A:
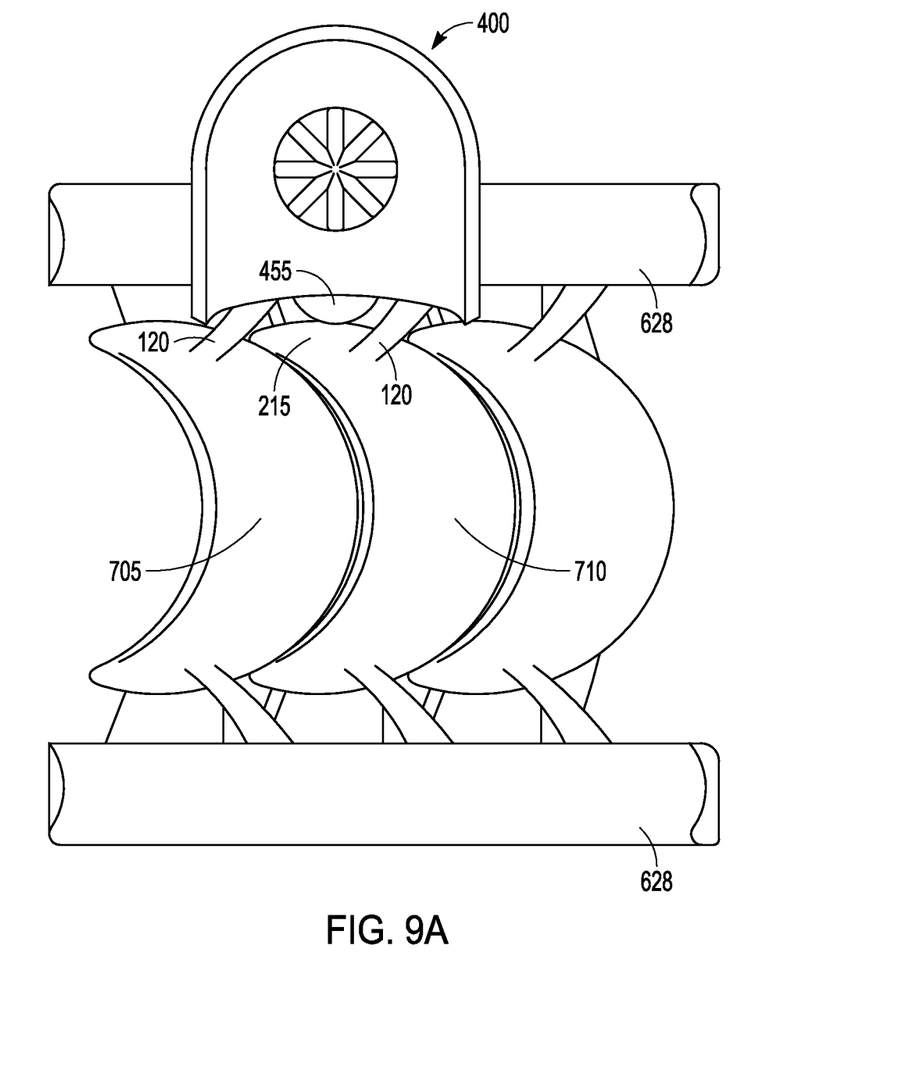
FIGS. 9A, 9B, and 9C are top, front elevation, and side elevation views respectively of a spine with medial/lateral blade installed according to an example embodiment.
Figure 9B:
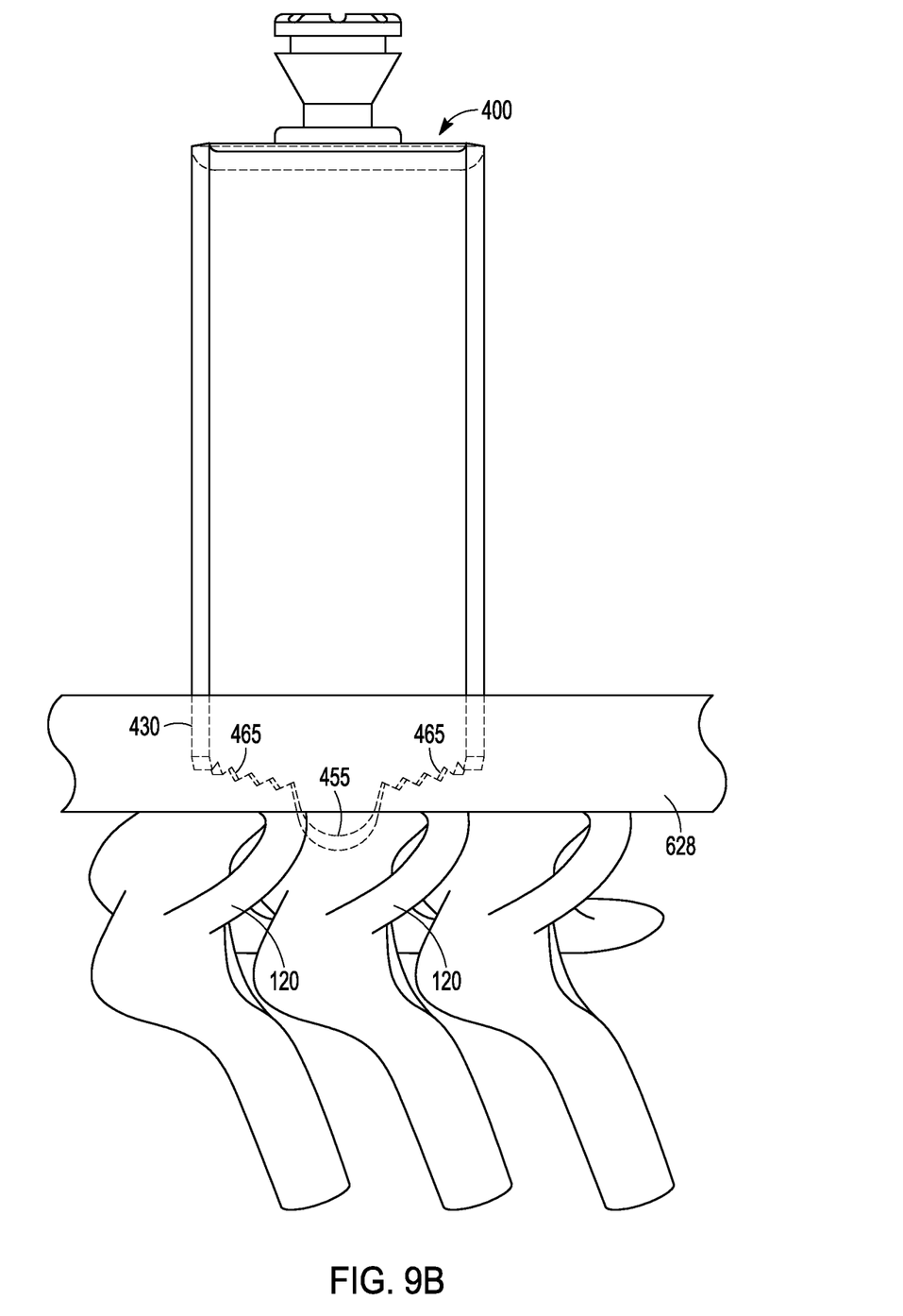
Figure 9C:
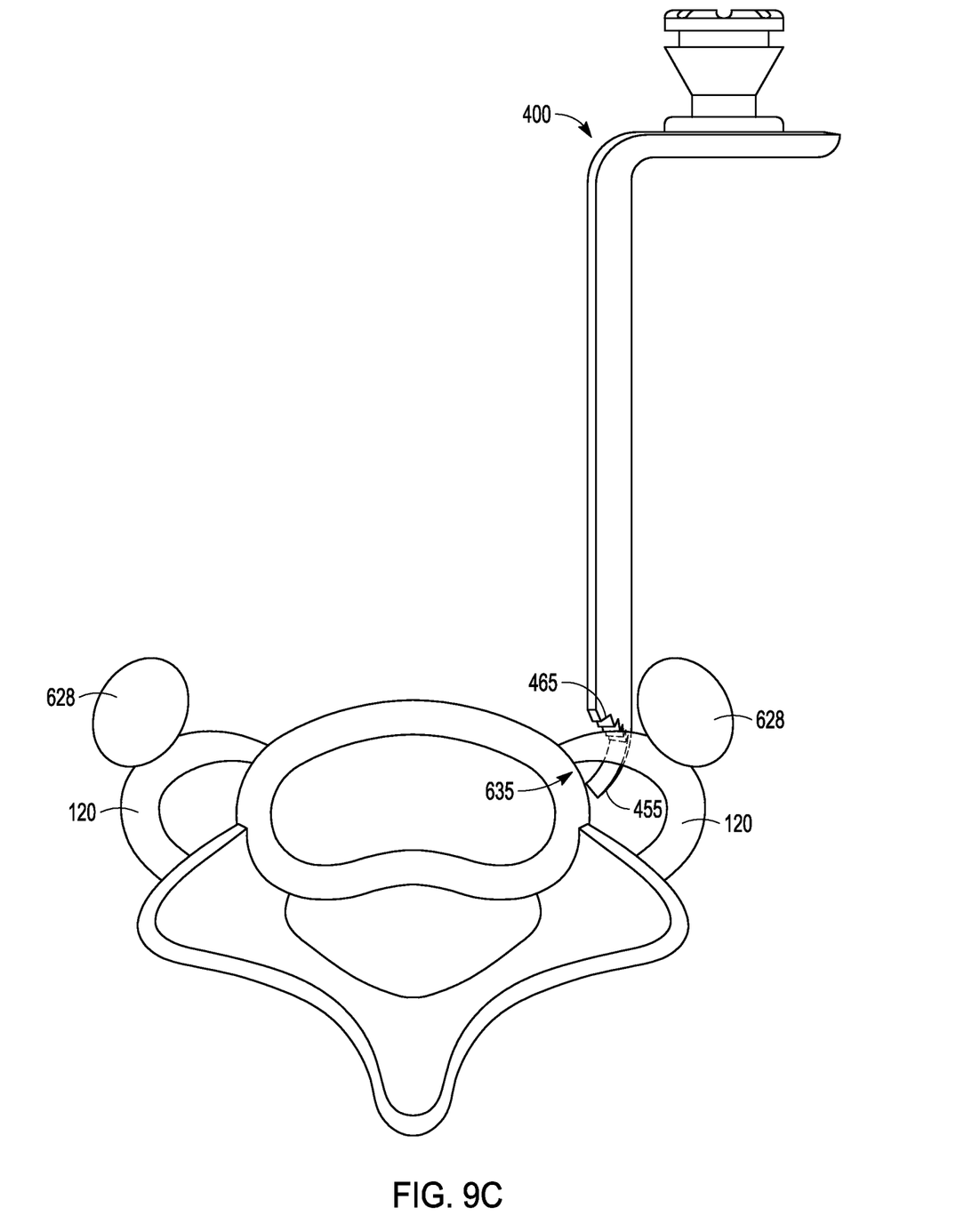

FIGS. 9A, 9B, and 9C are top, front elevation, and side elevation views respectively of a spine with blade 400 installed and showing additional detail. Reference numbers are consistent with reference numbers used in previous figures to identify like elements. FIG. 9A is situated such that the cranial side is on the left and caudal side on the right. FIG. 9B illustrates a sagittal side view, while FIG. 9C is a caudal end view.

Figure 10:
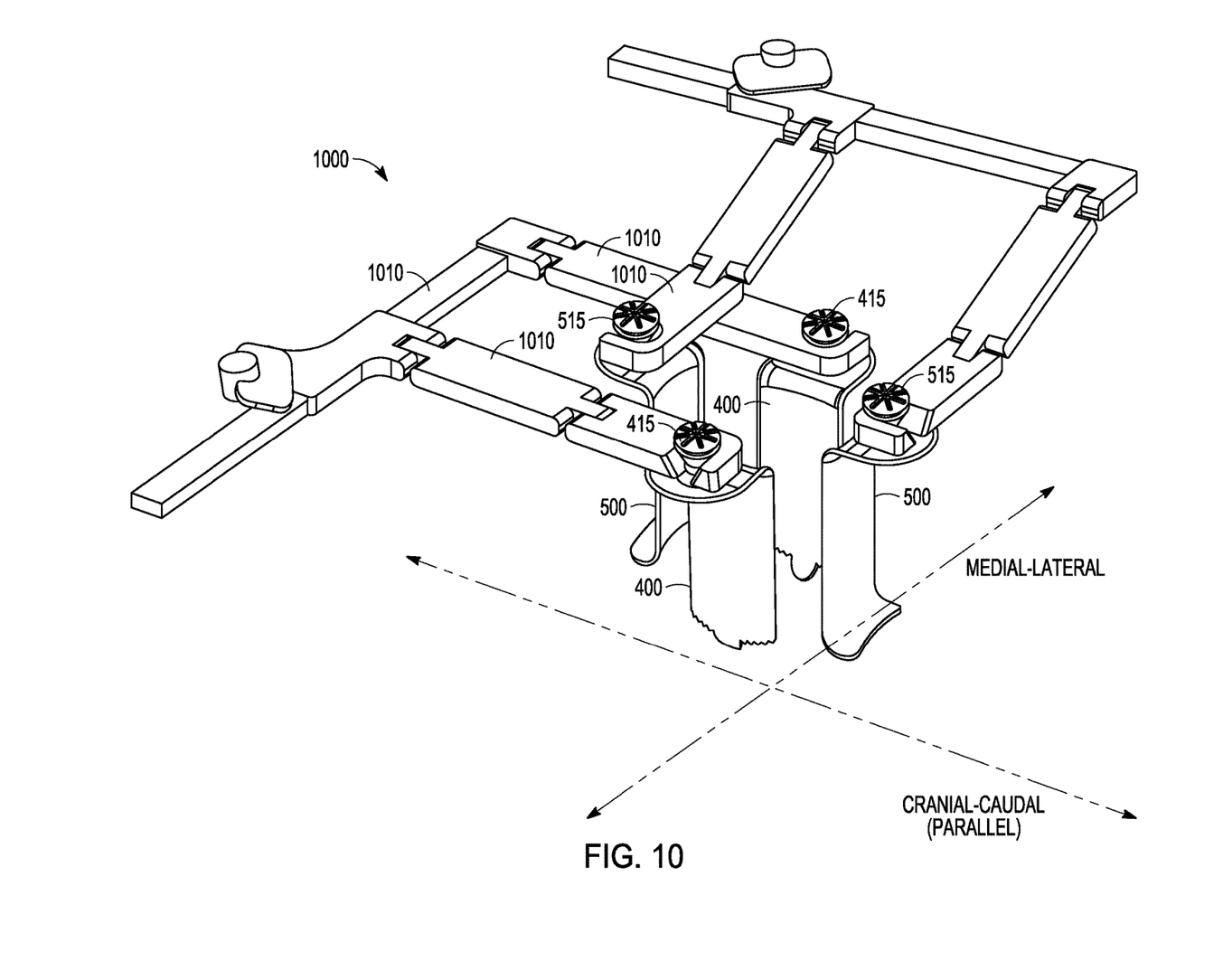
FIG. 10 is a perspective view of an example frame having multiple arms for attaching blades according to an example embodiment.

FIG. 10 is a perspective view of an example frame 1000 having multiple arms 1010 for attaching blades 400 and 500 via their respective pins 415 and 515. The arms may be adjustable in some embodiments to control the size of the surgical opening once blades are placed in retentive contact with desired portions of the spine.

Although a few embodiments have been described in detail above, other modifications are possible. Components may be added to or removed from, the described devices. One or more of the described blades may be used with other blades in further embodiments to provide the surgical corridor. Other embodiments may be within the scope of the following claims.

What is claimed is:

1. A retractor blade comprising:
    a shaft having a head portion at a first end and a foot portion at a second end of the shaft;
    a connector coupled to the head portion for coupling to a frame;
    a toe portion extending from the foot portion having a width and longitudinal curvature configured to at least partially conform to a curvature of a spinal vertebral body, wherein the toe portion comprises a semielliptical protuberance and a distal end of the toe portion opposite the head portion is rounded, and
    bridge portions, extending from lateral edges of the foot portion to lateral edges of the toe portion, wherein distal ends of the bridge portions are textured.

2. The retractor blade of claim 1 wherein the longitudinal curvature of the toe portion longitudinal curvature is configured to engage the uncinate process and uncal vertebral joint between adjacent vertebra.

3. The retractor blade of claim 1 wherein the shaft and toe portion have a transverse concave front surface and convex back surface.

4. The retractor blade of claim 3 wherein a curvature of the convex back surface increases proximate lateral edges of the convex back surface.

5. The retractor blade of claim 1 wherein the toe portion is centrally located between the lateral edges of the shaft and the bridge portions.

6. The retractor blade of claim 1 wherein the texture comprises triangular shaped teeth.

7. The retractor blade of claim 1 wherein the distal ends of the bridge portions extend toward the toe portion at an angle of between 60 and 100 degrees from a centerline of the shaft.

8. The retractor blade of claim 1 wherein shaft, including the head and foot portions has a length of between 30 to 70 mm.

9. The retractor blade of claim 1 wherein the shaft has a width of approximately 25 mm.

10. A retractor blade comprising:
   a shaft having a head portion at a first end and a foot portion at a second end of the shaft, wherein the shaft and foot portion have a transverse concave front surface and convex back surface;
   a connector pin coupled to the head portion for coupling to a frame;
   a toe portion extending from the foot portion having a width longitudinal curvature configured to at least partially engage a curvature of a spinal vertebral body, wherein the longitudinal curvature of the toe portion is configured to engage the uncinate process and uncal vertebral joint between adjacent vertebra, and wherein the toe portion comprises a semielliptical protuberance and a distal end of the toe portion opposite the head portion is rounded; and
   bridge portions, extending from lateral edges of the foot portion to lateral edges of the toe portion and configured to engage the transverse processes of adjacent vertebra, wherein distal ends of the bridge portions are textured.

11. The retractor blade of claim 10 wherein a curvature of the convex back surface increases proximate lateral edges of the convex back surface.

12. The retractor blade of claim 10 wherein the texture comprises triangular shaped teeth.

13. The retractor blade of claim 10 wherein the distal ends of the bridge portions extend toward the toe portion at an angle of between 60 and 100 degrees from a centerline of the shaft.

* * * * *